US010246400B2

(12) United States Patent
Fretta et al.

(10) Patent No.: US 10,246,400 B2
(45) Date of Patent: Apr. 2, 2019

(54) METHOD FOR THE PREPARATION OF (S)-2-ACETYLOXYPROPIONIC ACID AND DERIVATIVES THEREOF (71) Applicant: BRACCO IMAGING S.P.A., Milan (IT)

(72) Inventors: Roberta Fretta, Collegno (IT); Pietro Delogu, Trieste (IT); Fernanda Di Giorgio, Pradamano (IT); Alfonso Nardelli, Cervignano del Friuli (IT); Stefano Sguassero, San Giorgio di Nogaro (IT); Carlo Felice Viscardi, Milan (IT)

(73) Assignee: Bracco Imaging S.P.A., Milan (IT)

( * ) Notice: Subject to any disclaimer, the term of this patent is extended or adjusted under 35 U.S.C. 154(b) by 0 days.

(21) Appl. No.: 15/946,204

(22) Filed: Apr. 5, 2018

(65) Prior Publication Data
US 2018/0222840 A1 Aug. 9, 2018

Related U.S. Application Data (63) Continuation of application No. 15/315,401, filed as application No. PCT/EP2015/062892 on Jun. 10, 2015, now Pat. No. 9,963,416.

(30) Foreign Application Priority Data

Jun. 10, 2014 (EP) .................................. 14171751

(51) Int. Cl.
*C07C 67/08* (2006.01)
*C07C 67/287* (2006.01)
*C07C 51/44* (2006.01)
*B01D 3/00* (2006.01)
*C07C 67/54* (2006.01)

(52) U.S. Cl.
CPC .............. *C07C 67/08* (2013.01); *B01D 3/009* (2013.01); *C07C 51/44* (2013.01); *C07C 67/287* (2013.01); *C07C 67/54* (2013.01); C07B 2200/07 (2013.01)

(58) Field of Classification Search
CPC ....... C07C 51/44; C07C 67/08; C07C 67/287; C07C 59/08; C07C 69/14; C07C 69/63; C07C 67/54; B01D 3/009; C07B 2200/07
See application file for complete search history.

(56) References Cited

U.S. PATENT DOCUMENTS

| 2,399,595 | A | * | 4/1946 | Filachione | .............. | C07C 69/22 560/266 |
| 2,410,740 | A | | 11/1946 | Jones | | |
| 3,219,551 | A | | 11/1965 | Carel et al. | | |
| 5,362,905 | A | | 11/1994 | Villa et al. | | |
| 5,672,753 | A | | 9/1997 | Drauz et al. | | |
| 7,667,068 | B2 | | 2/2010 | Miller et al. | | |
| 2004/0110974 | A1 | * | 6/2004 | Lilga | ..................... | C07C 51/377 554/161 |
| 2011/0251420 | A1 | | 10/2011 | Disteldorf et al. | | |
| 2013/0150619 | A1 | | 6/2013 | Miller et al. | | |

FOREIGN PATENT DOCUMENTS

| EP | 0773925 B1 | 2/2000 |
| EP | 2230227 A1 | 9/2010 |
| GB | 1472050 A | 4/1977 |
| WO | 1996-016927 A1 | 6/1996 |
| WO | 1996-036590 A1 | 11/1996 |
| WO | 1996-037458 A1 | 11/1996 |
| WO | 1996-037459 A1 | 11/1996 |
| WO | 1996-037460 A1 | 11/1996 |
| WO | 1997-047590 A2 | 12/1997 |
| WO | 1998-024757 A1 | 6/1998 |
| WO | 1998-028259 A1 | 7/1998 |
| WO | 1999-058494 A2 | 11/1999 |
| WO | 2012-155676 A1 | 11/2012 |
| WO | 2014-090650 A1 | 6/2014 |

OTHER PUBLICATIONS

Office Action for Chinese application No. 201580030779.4, dated Jul. 26, 2018 (with English translation), 11 pages.
Amberlyst(TM) 15WET Industrial Grade Strongly Acidic Catalyst for Catalysis and Separation technologies, Rohm&Haas, 2003, pp. 1-4.
Buisson, Didier et al., "Preparation and use of (S)-O-acetyllactyl chloride (Mosandl's reagent) as a chiral derivatizing agent", Tetrahedron Asymmetry, Pergamon Press LTD., Oxford, GB, 1999, vol. 10, No. 15, pp. 2997-3002, XP004179155, ISSN: 0957-4166, DOI:10.1016/S0957-4166(99)00285-2.
European Pharmacopeia, 7th Edition, "Iopamidol," Strasbourg:Council of Europe, 2010, pp. 2266-2268.
Hulst, Ron, et al., "The Rational Design and Application of New Chiral Phosphonates for the Enantiomeric Excess Determination of Unprotected Amino Acids. Remarkable pH Dependency of the Diastereomeric Shift Differences," Tetrahedron, 1994, vol. 50, No. 40, pp. 11721-11728, XP002710428.
NIST Chemistry WebBook, SRD 69 ("Acetic Anhydride" entry, downloaded from http://webbook.nist.gov/cgi/cbook.cgi?ID=C108247&Mask=8 on Jul. 24, 2017, pp. 1-6).
O'Neil et al. (Editors), The Merck Index, XIII Edition, 2001, No. 5073, p. 909, Merck & Co., Inc., Whitehouse Station, NJ.

(Continued)

*Primary Examiner* — Yevgeny Valenrod
*Assistant Examiner* — Blaine G Doletski
(74) *Attorney, Agent, or Firm* — Guyan Liang (57) ABSTRACT The present invention relates to a method for the acetylation of an aqueous solution of lactic acid to (S)-2-acetyloxypropionic acid.

The process comprises in particular removing water from the solution of lactic acid and reacting lactic acid with acetic anhydride in the presence of acetic acid.

18 Claims, 7 Drawing Sheets

(56) References Cited

OTHER PUBLICATIONS

Testa, Emilio Von et al., "Zur Chemie der 3,3-Disubstituierten Azetidine, III", Justus Liebigs Annalen Der Chemie, Verlag Chemie GMBH, Weinheim, DE, 1962, vol. 660, pp. 135-143, XP002710427 (with English translation).
Tham, M.T., "Basic Distillation Equipment and Operation", Distillation, 2009, http://lorien.ncl.ac.ul/ming/distil/distileqp.htm, 2 pages.
Watson, Paul D., "Composition of Lactic Acid," Industrial and Engineering Chemistry, 1940, 32(3):399-401.
Zhang, Jun-hui et al., "Studies on the synthesis of Iopamidol", Fine and Specialty Chemicals, 2011, pp. 26-29 (with English translation).
Office Action for U.S. Appl. No. 14/650,868, dated Jul. 27, 2017, 48 pages.
Office Action for Chinese application No. 201380065023.4, dated May 4, 2016 (English translation), 6 pages.
Office Action for Chinese application No. 201380065023.4, dated Jan. 20, 2017 (English translation), 8 pages.
Office Action for Israeli application No. 239,328, dated Apr. 20, 2016, 3 pages.
Office Action for Korean application No. 10-2015-7017544, dated Apr. 20, 2017 (English translation), 10 pages.
European Search Report for European application No. 14171751.2, dated Nov. 27, 2014, 6 pages.
PCT International Search Report and Written Opinion for PCT/EP2013/075489, dated Feb. 7, 2014, 10 pages.
PCT International Search Report & Written Opinion of the International Searching Authority for PCT/EP2015/062892, dated Aug. 20, 2015, 13 page.
Office Action for Australian application No. 2015273640, dated Sep. 25, 2018, 4 pages.

\* cited by examiner

METHOD FOR THE PREPARATION OF (S)-2-ACETYLOXYPROPIONIC ACID AND DERIVATIVES THEREOF

CROSS-REFERENCE TO RELATED APPLICATIONS

This application is a continuation of co-pending U.S. patent application Ser. No. 15/315,401, filed Dec. 1, 2016, which is a 371 National Stage Application of corresponding International Application Number PCT/EP2015/062892, filed Jun. 10, 2015, now expired, which claims priority to and the benefit of European Application Number EP14171751.2, filed Jun. 10, 2014, now abandoned, all of which are hereby incorporated by reference in their entirety.

The present invention relates to a process for the preparation of a key reagent in the synthesis of contrast agents for X-ray iodinated compounds.

BACKGROUND OF THE INVENTION

Iopamidol (The Merck Index, XIII Ed., 2001, No. 5073) (N,N'-Bis[2-hydroxy-1-(hydroxymethyl)ethyl]-5-[[(2S)-2-hydroxy-1-oxopropyl]-amino]-2,4,6-triiodo-1,3-benzenedicarboxamide, is a contrast agent widely used for diagnostic investigations by X-ray.

Its synthesis is known since the eighties and disclosed e.g. in GB1472050. Since then, alternative processes for its preparation have been developed, for example starting from 5-nitroisophthalic acid, suitably reduced to the corresponding amino derivative, for example by means of catalytic hydrogenation, and after that iodinated on the benzene ring so as to form the corresponding 2,4,6-triiodo derivative. This one, for example in the presence of thionyl chloride, is then converted into the corresponding dichloride of 5-amino-2,4,6-triiodoisophthalic acid (see i.e.: WO 96/037458, WO 96/037459, WO 96/016927 e WO 96/036590).

The process for Iopamidol synthesis from the dichloride of 5-amino-2,4,6-triiodoisophthalic acid (I) and its variants (see for example: WO 96/037460, U.S. Pat. No. 5,362,905, WO 97/047590, WO 98/24757, WO 98/028259 and WO 99/058494) may be schematically represented as follows:

(I) is converted into the corresponding compound of formula (II) in the presence of (S)-2-acetyloxypropionyl chloride. The so prepared intermediate compound of formula (II) is then converted into the acetyl-Iopamidol of formula (III) in the presence of 2-amino-1,3-propandiol (serinol).

At the end, the hydrolysis of the compound of formula (III) and the subsequent purification of the obtained product allow to isolate Iopamidol, compound of formula (IV) (European Pharmacopoeia 6.0 Ed. January 2008: 1115).

Even if different process variants have been disclosed and used for Iopamidol preparation, one of the key reagents, common to all the synthesis, is still the (S)-2-acetyloxypropionyl chloride, the purity of which is crucial to achieve the Pharmacopoeia requirements on the final end product.

The preparation of this reagent is disclosed for example in EP773925, where the starting reagent is sodium lactate, in the presence of HCl and acetic anhydride, in acetic acid; the so obtained (S)-2-acetyloxypropionic acid intermediate is then chlorinated with thionyl chloride to give the corresponding (S)-2-acetoxypropionyl chloride. Sodium lactate, commercially available but quite expensive, has to be transformed in situ, at first, into lactic acid by adding hydrochloric acid gas and then acetylated. The addition of HCl leads to the formation of sodium chloride that has to be removed by mechanical means, usually by filtration. These steps have been summarized in EP2230227 (prior art discussion).

The prior art also discloses few variants of the (S)-2-acetyloxypropionic acid synthesis and its chlorination. For example, Zhang 3. et al. Fine and Specialty Chemicals, 2011, 6:26-29, discloses the preparation of (S)-2-acetyloxypropionyl chloride starting from lactic acid, using acetyl chloride as an acetylating agent. The low yields do not allow an industrial scale development.

WO2012/155676 discloses the synthesis of (S)-2-acetyloxypropionic acid from lactic acid (85%) in toluene, in the presence of acetic acid and sulfuric acid as catalyst, the reaction requires several hours at reflux.

U.S. Pat. No. 2,399,595 describes some approaches to the synthesis of (S)-2-acetyloxypropionic acid by reacting pure lactic acid, with various mixtures of acetic acid and/or acetic anhydride, typically in the presence of acid catalysts (HCl or sulfuric acid) and/or organic solvents (benzene). In the only example where an aqueous solution (80%) of lactic acid is used, this is reacted with acetic acid in the presence of benzene and concentrated sulfuric acid.

US 2004/0110974 describes the synthesis of (S)-2-acetyloxypropionic acid from 85% lactic acid in acetic acid and with $H_2SO_4$ in a continuous mode; water is removed by acetic acid, which is also used as the acetylating agent. According to this process, a large excess of acetic acid is used to minimize dimerization.

WO 2014/090650 discloses a process for preparing (S)-2-acetyloxypropionic acid which comprises distilling water from an aqueous solution of lactic acid with a counter stream of acetic acid continuously fed into the system, reacting lactic acid in acetic acid with acetic anhydride and recovering the (S)-2-acetyloxypropionic acid by distillation of acetic acid.

The Applicant has now found a new method for preparing (S)-2-acetyloxypropionic acid wherein the sole reactants employed are an aqueous solution of lactic acid and acetic anhydride. The preparation method comprises in particular introducing only acetic anhydride and substantially anhydrous lactic acid in the reaction environment of a preparation assembly, while acetic acid is formed in situ (essentially as a by-product of the acetylation reaction between acetic anhydride and lactic acid). According to the invention, the acetic acid formed in situ is advantageously employed as a vapour stream for stripping water from the lactic acid solution fed into the preparation assembly, in order to provide the desired essentially anhydrous lactic acid to the reaction environment.

SUMMARY OF THE INVENTION

An aspect of the present invention thus relates to a method for the preparation of (S)-2-acetyloxypropionic acid in a preparation assembly comprising a distillation section (A) and a reaction section (B), the distillation section (A) comprising a top portion and a bottom portion connected to said reaction section (B), the method comprising the steps of:
a. continuously feeding an aqueous solution of lactic acid to the top portion of the distillation section (A);
b. feeding acetic anhydride into the reaction section (B);
c. reacting lactic acid with acetic anhydride in the reaction section (B), thus forming (S)-2-acetyloxypropionic acid and acetic acid;
d. evaporating a mixture of the formed acetic acid and of unreacted acetic anhydride from reaction section (B);
e. feeding the vaporized mixture of step d to distillation section (A) for stripping water from the aqueous solution of lactic acid which counterflows through said distillation section (A) towards reaction section (B), so that a mixture of substantially anhydrous lactic acid and acetic acid enters the reaction section (B) from the bottom portion of the distillation section (A);
f. recovering (S)-2-acetyloxypropionic acid from the reaction section (B);
g. collecting a diluted aqueous solution of acetic acid at the top portion of the distillation section (A).

According to a preferred embodiment, section (B) of the assembly comprises two separate sub-sections (B') and (B"), wherein sub-section (B') is essentially dedicated at performing the reaction between lactic acid and acetic anhydride, while sub-section (B") is essentially dedicated at evaporating acetic acid and unreacted acetic anhydride and feeding to the distillation section A.

The so obtained (S)-2-acetyloxypropionic acid may then be subjected to any chlorination reaction according to the art, to obtain the desired (S)-2-acetyloxypropionyl chloride.

DETAILED DESCRIPTION OF THE INVENTION

The following reaction scheme illustrates the reaction between lactic acid and acetic anhydride, to provide (S)-2-acetyloxypropionic acid and acetic acid as by product:

While apparently rather simple on the paper and to some extent at laboratory scale, the synthesis (S)-2-acetyloxypropionic acid of L-lactic acid becomes extremely complex when moving to large-scale production, particularly when aqueous solutions of lactic acid are used as starting material.

As a matter of fact, in order to produce high amounts of (S)-2-acetyloxypropionic acid of high standard quality, both the preliminary removal of water and the acetylation reaction are critical. In fact, the possible concurrent lactic acid polymerization, greatly reducing the yields and giving by-products that must be cleared off, has to be avoided, to avoid important economic and environmental burden.

In particular, commercial lactic acid is commonly available on industrial scale as an aqueous solution (commercially available generally in 30%, 50% or 88-90% concentrations). As observed by the Applicant, water has to be removed before adding acetic anhydride into the reaction environment, to avoid reaction of acetic anhydride with water, which would greatly increase the amount of acetic anhydride needed to complete the reaction. This removal cannot however be accomplished by simple water distillation, as lactic acid condensates to its dimer at the conditions applied during distillation (namely high temperatures and elevated concentrations of lactic acid), thus reducing yield and purity of the final product.

The preparation method of the present invention allows accomplishing L-lactic acid acetylation with acetic anhydride while taking particular advantage from the acetic acid evolved by the reaction as secondary product, in order to remove water and avoiding lactic acid dimerization and acetic anhydride hydrolysis, as described in full detail below.

Figure 1:
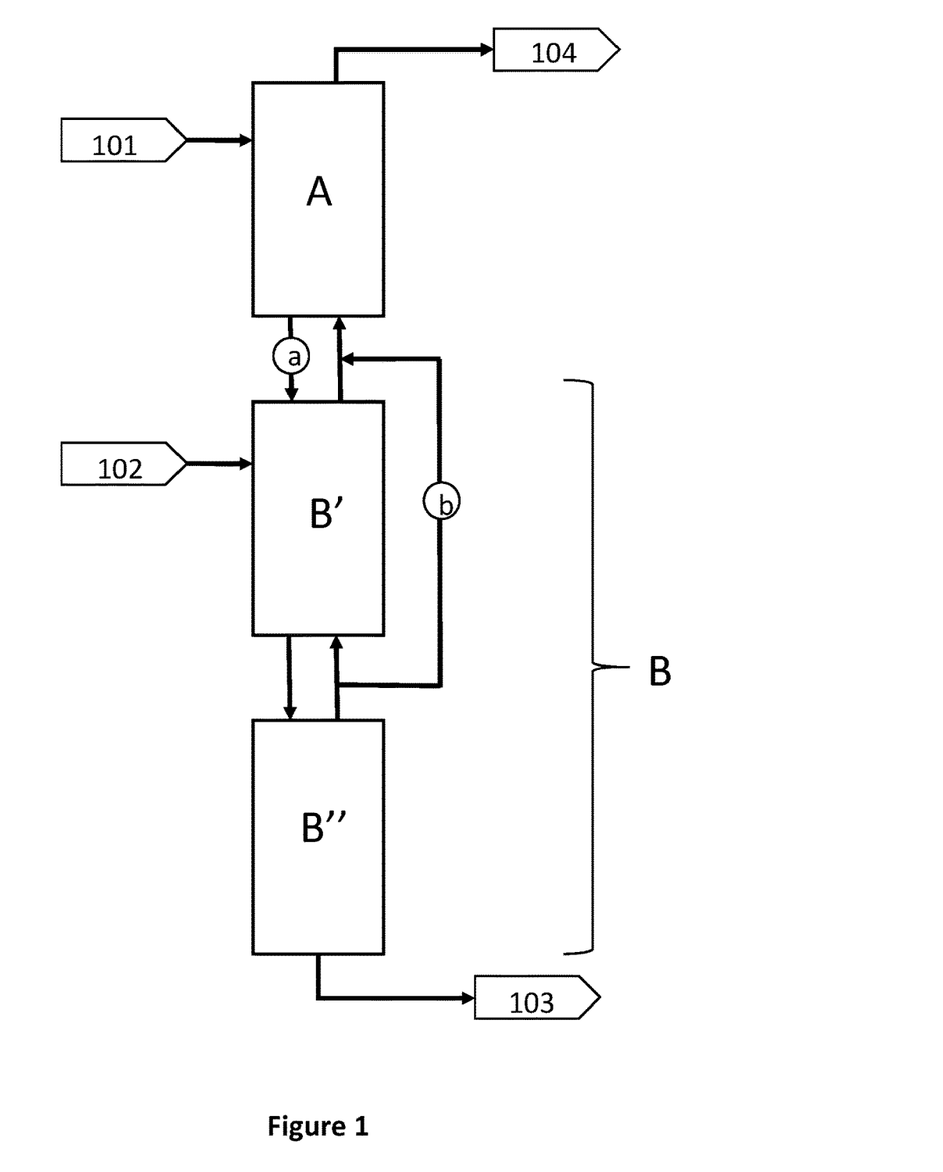
FIG. 1 represents a schematic drawing of the general principles of the process and assembly for performing the method of the invention.

FIG. 1 shows a schematic drawing of a preparation assembly for performing the process according to the invention, where distillation section (A) and reaction section (B), as well as subsections B' and B", are identified together with the respective main flows of materials.

Distillation section (A), which may typically comprise a distillation column, is continuously fed from the top with an aqueous solution of lactic acid 101. The method of the present invention allows using commercial lactic acid solution, i.e. those available at a concentration comprised from 20 to 90% (w/w), preferably lower than about 60% (as at higher concentration, these solutions may contain undesirably high amounts of lactic acid in dimeric form). More preferably a 40% to 50% (w/w) aqueous solution of lactic acid is used. The distillation column is preferably equipped with a suitable number of distillation trays (e.g. at least five trays) or with packing materials.

Depending on the specific embodiment, the reaction section (B) may form an integral part with the distillation section (A) (as illustrated e.g. more in detail in FIG. 2) or, preferably, it forms an independent element of the preparation assembly.

Acetic anhydride 102 is fed into reaction section (B), particularly in sub-section (B') which is essentially dedicated to perform the reaction between acetic anhydride and lactic acid, this latter flowing into the reaction section B together with acetic acid from the bottom of section (A) as a liquid mixture (indicated by arrow "a" in the scheme). The molar ratio between acetic anhydride and lactic acid is preferably comprised in the range of from 1.01 to 1.5, more preferably from 1.05 to 1.25. The feeding of acetic anhydride may be continuous or discontinuous, as illustrated more in detail in the specific embodiments.

The reaction conditions (in particular temperature and concentration of lactic acid) are such that the undesired dimerization of lactic acid is minimized. The reaction temperature is thus preferably from 50° C. and 100° C., more preferably from 60° to 80° C. The concentration of lactic acid in the liquid mixture flowing into the reaction section B from the bottom of section (A) is preferably kept below 60% (w/w), more preferably between 15% and 50% (w/w) and even more preferably between 20% and 40% (w/w).

Reaction section (B), and particularly sub-section B', comprises suitable means for performing the reaction, preferably a stirred tank reactor and/or a plug flow reactor, optionally in combination with a reactor pump.

Reaction section (B) may further comprise a fixed bed of a solid acidic catalyst, with cation exchanging groups bound to a solid phase, i.e. a matrix, either polymeric or reticular which is inert in the harsh conditions of the acetylation reaction. Preferred acidic catalysts are the Brønsted or the Lewis acids in the solid phase. In particular, among the first type, cation resins are preferred, even more preferably sulfonic resins in the acidic form, such as for example Amberlyst™ 15 Dry, which is the most preferred. Zeolites and montmorillonites belong to the second type of heterogeneous acidic catalysts, such as for example Montmorillonit K10 and Nafion™, Montmorillonit NR 50. Amberlyst™ 15 Dry type resins are preferred as they are commercially available in an anhydrous form. Other strong cationic resins with a reticular type-like matrix, in their dry form may be used with comparable results. Catalyst pellets may be supported by a horizontal grid in a vessel which is fed from the top and discharged from the bottom.

Reaction section (B) is preferably designed to allow sufficient liquid hold-up to provide for completion of the acetylation reaction before the mixture reaches sub-section B". This is achieved by either a suitable design of the internals of the column and/or by adding reaction devices outside the column(s) (as illustrated for instance in FIGS. 4 and 5). Liquid hold-up inside the column may be obtained applying any of the internals well known to any person skilled in distillation and rectification, such as increasing the height of tray weirs, and/or inserting chimney trays. Chimney trays are preferably equipped with parallel weirs designed to force the liquid along a folded channel. Alternatively, the desired liquid hold-up can be obtained by a suitable design of the reaction section B by using reaction/evaporation tanks disposed in parallel, as illustrated for instance in FIGS. 6 and 7.

Sub-section (B"), connected to sub-section (B') with which it may optionally form an integral part, is essentially dedicated to the evaporation of acetic acid and unreacted acetic anhydride by means of any suitable evaporating means, e.g. a reboiler, optionally in combination with a distillation column. The vapor outlet of sub-section B" may be connected either to sub-section B' (so that the vapors first pass through the reaction environment and then go to the distillation section (A)) or, preferably, it is directly connected to the distillation section A (arrow "b" in the scheme). According to an embodiment of the invention, the vapors may be fed to the bottom of section A from both sub-section B' and sub-section B". As the skilled person will appreciate, the temperatures in the evaporation step may depend from many parameters, including the specific design of the device used in sub-section B", the negative pressure applied thereon and the progress of the evaporation step, as indicated in more detail in the examples.

A vaporized mixture of the acetic acid formed in situ and of the excess of unreacted acetic anhydride, generated by the heat supplied to distillation sub-section (B"), along with the reaction heat evolved in sub-section (B'), flows from section B into section (A). Vaporized acetic acid progressively strips water from the aqueous solution of lactic acid which is continuously fed at the top of the distillation section (A), while the content of acetic anhydride in the vapors flowing upstream through the column is progressively decreased. In particular, a sufficient number of equilibrium contact stages (or theoretical trays) minimizes the direct contact between water and acetic anhydride (and therefore its hydrolysis) in the distillation section A in order to limit or substantially avoid the mixing of water with acetic anhydride in section A, while substantially preventing water from entering the reaction section B. At the exit of the bottom part of the distillation section substantially anhydrous lactic acid (typically with a water content of less than 1% w/w, preferably less than 0.5% w/w and even more preferably less than 0.1% w/w) thus flows into the reaction section B, together with refluxed acetic acid and acetic anhydride. As previously mentioned, the concentration of lactic acid in the liquid mixture flowing from distillation section A into reaction section B is preferably controlled in order to minimize the undesirable formation of by-products (in particular dimeric lactic acid). Substantially pure (S)-2-acetyloxypropionic acid (103) is then recovered from the bottom of section B, particularly sub-section B", while the water from the aqueous solution of lactic acid is collected as a diluted aqueous solution of acetic acid (104) at the top of section (A), by any suitable means, e.g. by means of a condenser. The amount of collected acetic acid is approximately equimolar with respect to the amount of lactic acid fed into the assembly, particularly when the acetic anhydride is used in equimolar amount or in a slight excess with respect to lactic acid. In preferred embodiments, the substantial totality of the acetic acid formed in situ is evaporated while the substantial totality of the excess of acetic anhydride is not hydrolyzed and is thus refluxed into the reaction section. The vapor outlet is preferably connected to a vacuum pump, in order to keep the preparation assembly under an overall negative pressure, preferably in the range of from 5 to 200 mbar, preferably between 10 and 100 mbar.

At the first start-up of the process, hold-ups of the preparation assembly are preferably filled with a small amount of acetic anhydride or acetic acid, essentially to avoid water reaching the reaction section (B) before the steady state conditions of the continuous process are reached. Subsequent restarts of the assembly do not generally require this preliminary filling, provided that the respective hold-ups of the assembly are not drained.

The method according to the present invention allows obtaining (S)-2-acetyloxypropionic acid in relatively high overall yields (typically at least 99%) and purity (typically about 93%, HPLC, the impurities being mainly represented by residual acetic acid and acetic anhydride and by the dimeric compounds already present in L-lactic acid aqueous solution used for the process).

These results are achieved by preventing yield losses derived from reaction between acetic anhydride and water and from lactic acid dimerization reaction, in the absence of any solvent or auxiliary material.

The following figures will illustrate in more detail some specific embodiments of the assembly for carrying out the preparation method of the invention.

Figure 2:
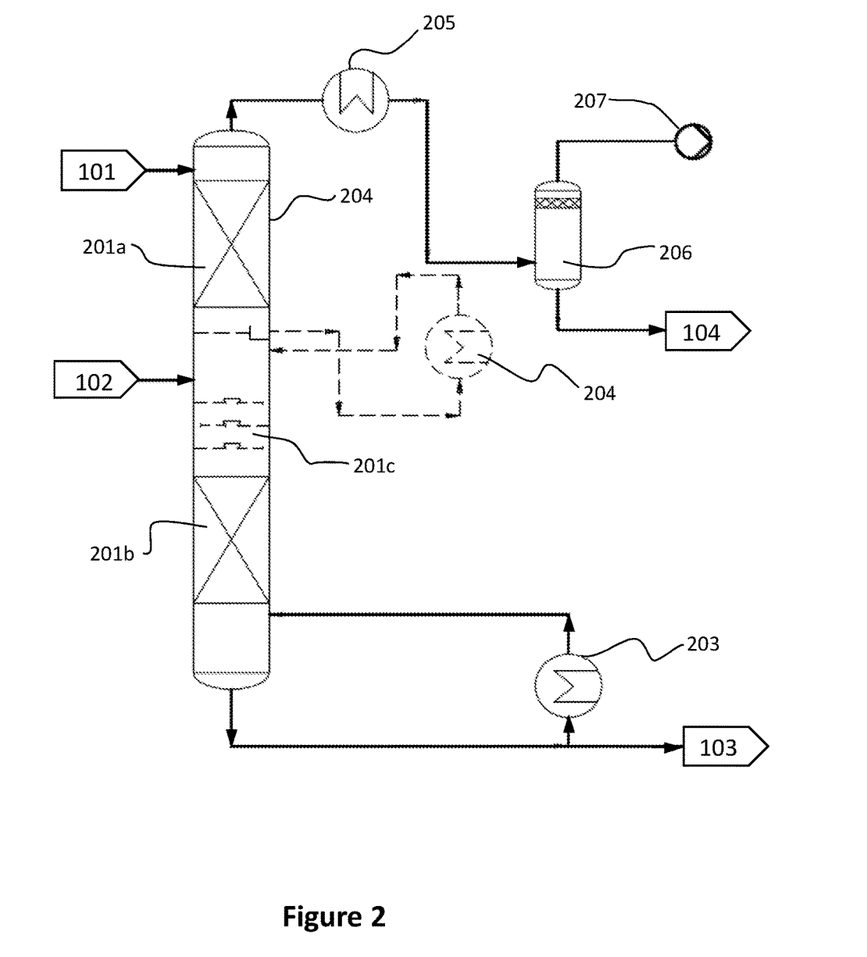
FIGS. 2 to 7 represent various embodiments of an assembly for performing the method of the invention.

FIG. 2 shows an embodiment of a preparation assembly suitable for a process according to the invention where the distillation section (A) and the reaction section (B) form an integral part. The assembly comprises in particular a distillation column 201 which is fed at the top with the solution of lactic acid 101 and at its middle section with acetic anhydride 102. The column preferably comprises in its lower section 201b (reaction section) a suitable internal material for facilitating/optimizing the reaction conditions and the evaporation of acetic acid and unreacted acetic anhydride (typically high hydraulic capacity structured packing made of suitable corrosion resistant material, e.g. graphite or metallic alloys, such as nickel-chromium-molybdenum-tungsten alloy). For instance, MellapakPlus™ with Hastelloy® C-22® can be used as structured packing. Liquid hold-up elements 201c (e.g. chimney trays) may also be provided in the middle section of column 201, while the upper section 201a (stripping section) contains means for optimizing the liquid/vapour contact and stripping water, such as high separation efficiency structured packing made of suitable corrosion resitant material, e.g. graphite, stainless steel or other metallic alloys, such as nickel-chromium-molybdenum-tungsten alloy; advantageously, the same MellapakPlus™ with Hastelloy® C-22® can be used as structured packing).

The assembly illustrated in FIG. 2 further comprises a reboiler 203 for heating the mixture at the bottom of column 201 and evaporating acetic acid and excess acetic anhydride therefrom. (S)-2-acetyloxypropionic acid 103 is recovered from the bottom of column 201 while acetic acid and water are evaporated from the top thereof by means of a system comprising a condenser 205, a condenser drum 206 and a vacuum pump 207, and finally discarded as an aqueous solution of acetic acid 104. Optionally, an additional reboiler 204 is connected to the column, in order to reduce the duty of reboiler 203.

Figure 3:
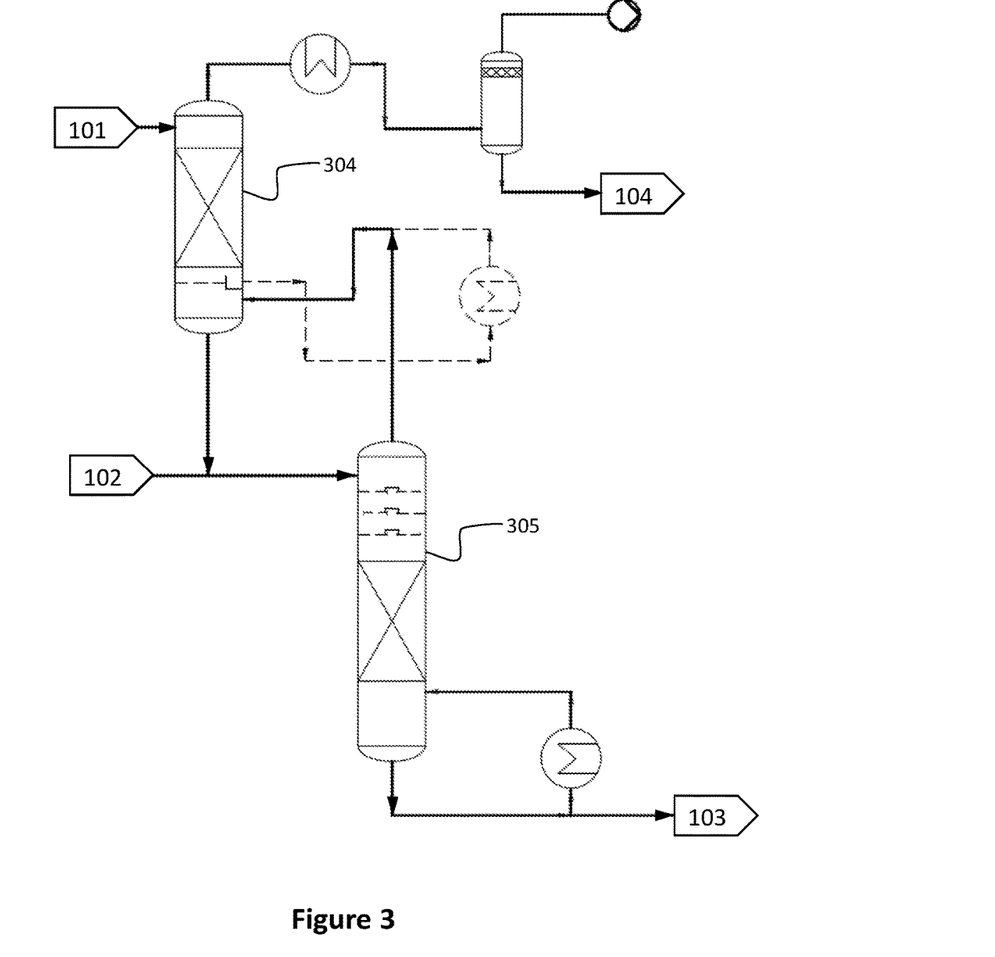

FIG. 3 shows an alternative embodiment of a preparation assembly illustrated in FIG. 2 where the distillation section (A) and the reaction section (B) are provided as separate elements. The assembly comprises in particular a distillation column 304 (distillation section) for the stripping of water from the aqueous solution of lactic acid 101, which is fed at the top of the column. The anhydrous lactic acid from the bottom of column 304 is fed together with acetic anhydride 102 at the top of column 305 (reaction section). In turn, acetic acid and acetic anhydride vapors exiting from the top of column 305 are fed to the bottom of column 304. The other elements and flows of the assembly are as illustrated in FIG. 2.

Figure 4:
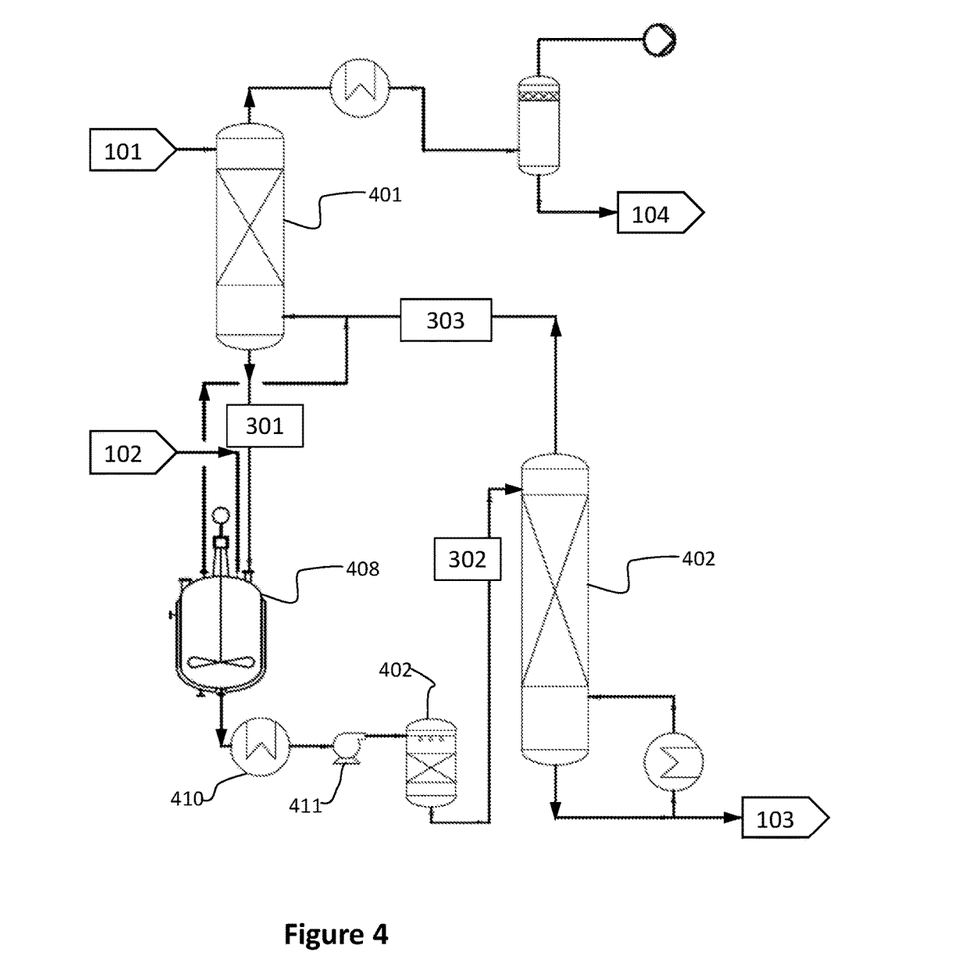

FIG. 4 shows an alternative embodiment of a preparation assembly where the reaction section B of the assembly is separated in two sub-sections B' and B". Sub-section B' comprises in particular a reactor tank 408 to which the mixture of lactic acid 101 and acetic acid (from the bottom of distillation column 401) are fed together with acetic anhydride 102. The reactor tank may be for instance a stirred jacketed reactor tank. The reaction mixture is fed to a fixed bed reactor 409 by means of reactor pump 411 after passing through a cooler 410 (which reduces the temperature of the mixture typically at about 35° C.-55° C.). Suitable resins for the fixed bed are those illustrated previously.

The reaction mixture from reactor 409 is then fed to the top of distillation column 402, where acetic acid and the excess of acetic anhydride are evaporated. The evaporated mixture is then fed from the top of column 402 to the bottom of distillation column 401 for the stripping of water from the counterflowing aqueous solution of lactic acid. Distillation column 401 is equipped with means for optimizing the liquid/vapour contact and stripping water, such as a high separation efficiency structured packing as previously mentioned. As shown in FIG. 4, the assembly may further comprise a pipe connecting the top of the reactor 408 with the bottom of column 401. In this way, a certain amount of acetic acid and of unreacted acetic anhydride may advantageously be evaporated directly from reactor tank 408 (e.g. from about 20% to about 50% w/w of the total evaporated amount) and fed to the bottom of distillation column 401.

As above, (S)-2-acetyloxypropionic acid 103 is thus recovered from the bottom of column 402 while acetic acid and water evaporate from the top of column 401 and are discarded as an aqueous solution of acetic acid 104.

Here and in the subsequent figures and examples, numbers 301, 302 and 303 identify the respective main streams of the process, i.e.: the liquid stream 301 of the mixture of lactic acid and acetic acid flowing from distillation section to reactor sub-section; the liquid stream 302 of the reaction mixture flowing from reactor sub-section to evaporation sub-section; and the vapor stream 303 flowing from evaporation sub-section to distillation section.

Figure 5:
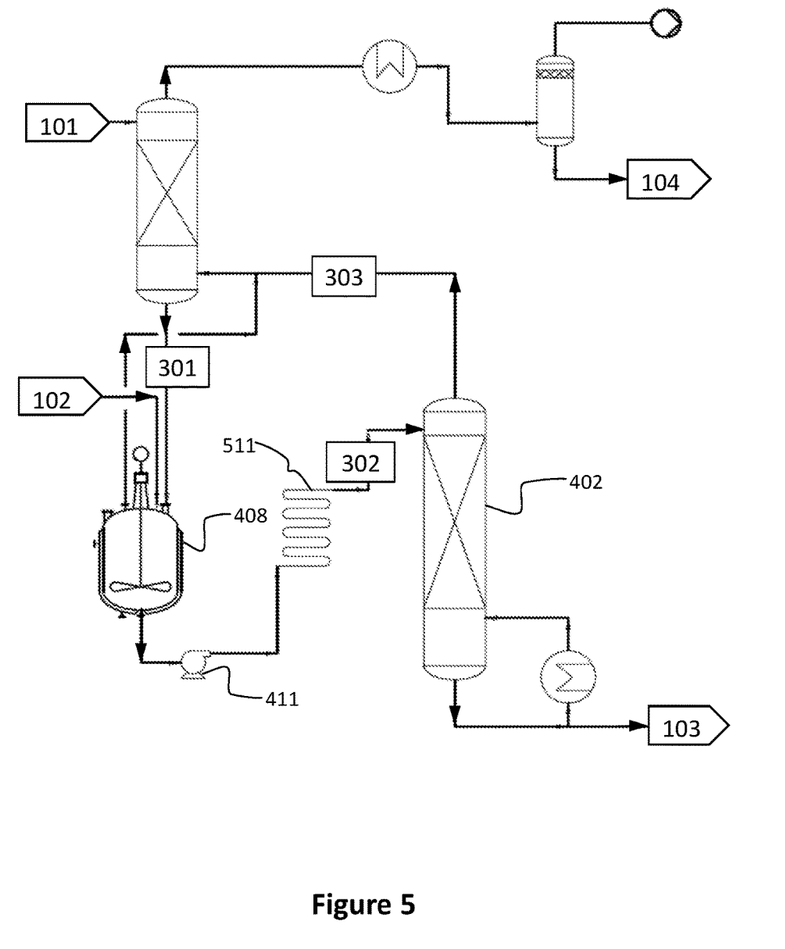

FIG. 5 shows an alternative embodiment of a preparation assembly of FIG. 4. Here the reaction sub-section B' comprises a reactor tank 408 as above described which is connected (through reactor pump 411) to a plug flow reactor 501 and then to evaporation column 402. The reminder of the assembly and of the flows of materials is as described in FIG. 4.

Figure 6:
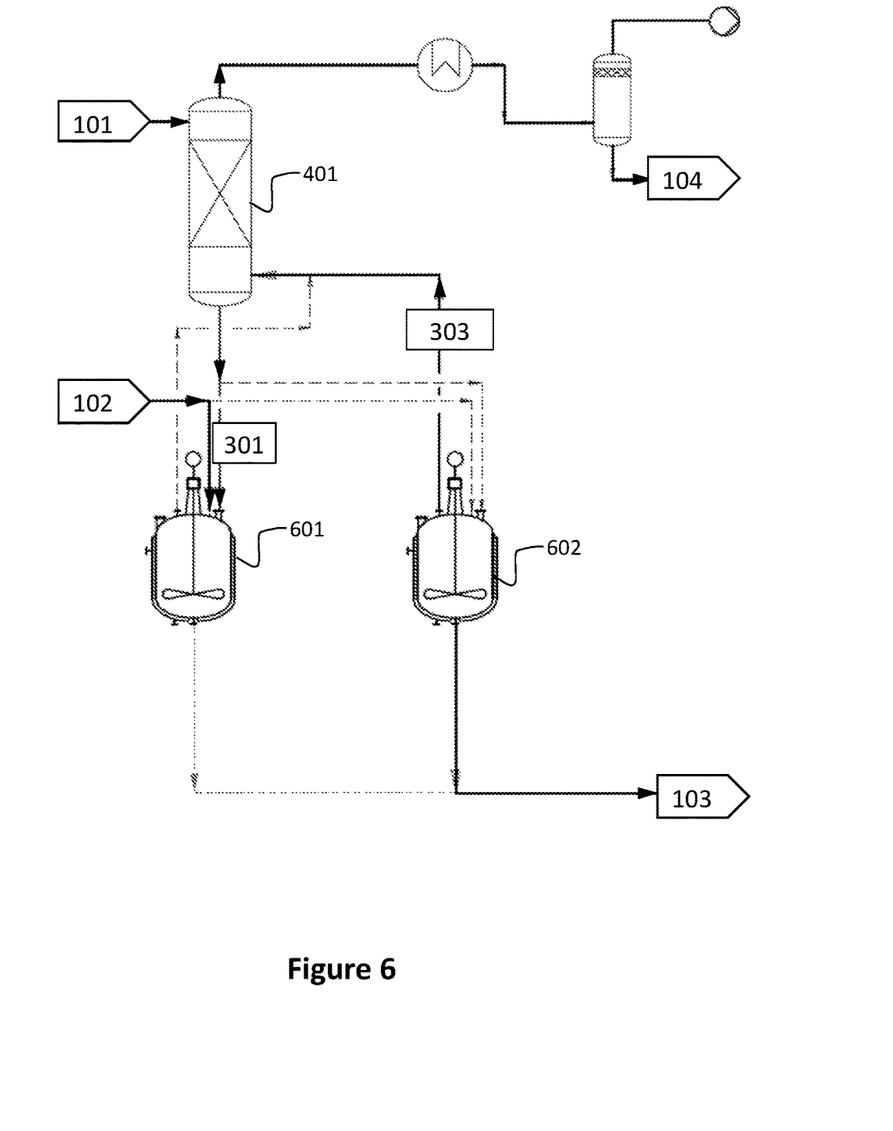

FIG. 6 shows a further embodiment where reaction sub-section B' and evaporation sub-section B" are represented in parallel as respective reaction tanks 601 and 602, preferably stirred jacketed reactor tanks. According to this embodiment, the two tanks may be used alternatively and interchangeably as reaction sub-section B' and evaporation sub-section B" for cyclically performing a process according to the invention, in combination with the distillation column 401. For the sake of clarity, in the drawing of FIG. 6, the solid arrows indicate pipelines where the main mass flow of the process occurs, while dotted arrows indicate pipelines where no or non-significant mass flow occurs.

In particular, according to a first cycle of the process, the first tank 601, which is continuously fed with a mixture of lactic acid and acetic acid from column 401 and with acetic anhydride 102 (bold arrows directed to tank 601) performs the acetylation reaction. Concurrently, the second tank 602 (which contains a mixture of a previous acetylation reaction substantially terminated) is essentially dedicated to the evaporation of acetic acid and unreacted acetic anhydride from the mixture. The evaporated mixture is thus fed from the top of tank 602 (solid arrow) to the bottom of distillation column 401, for stripping the water from the aqueous solution of lactic acid 101 which is continuously fed at the top of distillation column 401. In preferred embodiments, in addition to the main flow of the vaporized mixture of acetic acid and acetic anhydride from evaporation tank 602, also a certain amount of the vaporized mixture from reactor tank 601 (preferably from 15% to 40%, more preferably from 20 to 30% of the total vapor flow) is fed to the bottom of column 401 (dotted arrow from tank 601).

Once acetic acid and acetic anhydride are evaporated to the desired residual level from tank 602, (S)-2-acetyloxypropionic acid 103 can be recovered from the bottom of the tank. At this point a subsequent process cycle starts: by switching the valves controlling the loading pipelines, the lactic acid/acetic acid mixture together with acetic anhydride can be fed to tank 602, while tank 601 is now essentially dedicated to the evaporation of acetic acid and acetic anhydride.

As the functionality of the two tanks is fully interchangeable, the skilled person will appreciate that, while it is preferable to switch between the functions of the two tanks at the completion or close to the completion of the acetylation reaction, the switching may nevertheless be effected at any suitable progress stage of the acetylation reaction.

Figure 7:
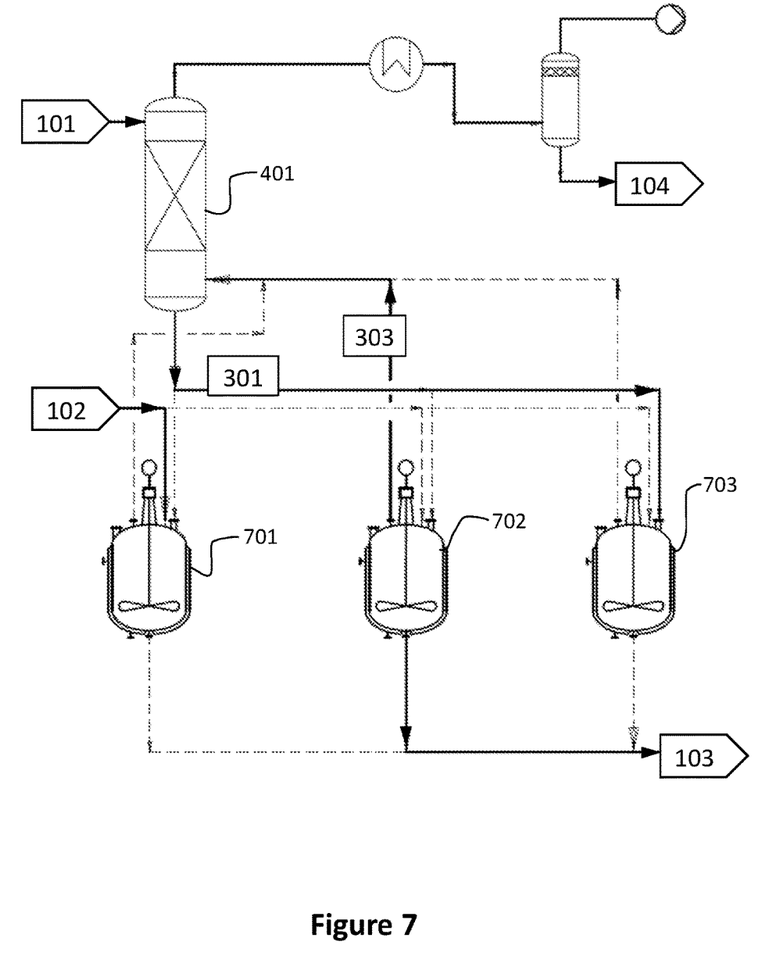

In order to better control the different functions of the tanks, it is preferable to employ more than two tanks, for instance three parallel tanks as illustrated in the embodiment of FIG. 7.

The assembly illustrated in FIG. 7 is essentially the same as the one illustrated in FIG. 6, with the only difference that it contains an additional tank 703.

According to a first cycle of this embodiment, the tank 701 ("reaction tank") is essentially dedicated at performing the acetylation reaction in batch mode. To this purpose, reactor 701 has been previously fed with the mixture of lactic acid and acetic acid from column 401 and with acetic anhydride 102. The second tank 702 ("evaporation tank") is essentially dedicated to the evaporation of the mixture of acetic acid and acetic anhydride from a completed reaction mixture; the mixture of vapors is continuously fed to the bottom of column 401. The third tank 703 ("collection tank") is then essentially dedicated at collecting the mixture of lactic acid and acetic acid continuously flowing from column 401. At the end of the process cycle (i.e. when the acetylation reaction in tank 701 is substantially completed or close to completion and the substantial totality of acetic acid and acetic anhydride have been evaporated from tank 702), (S)-2-acetyloxypropionic acid 103 can be recovered from the bottom of evaporation tank 702. The valves controlling the loading pipelines are thus switched to modify the respective functions of the three tanks for beginning a subsequent process cycle: tank 701 becomes essentially an "evaporation tank" for feeding column 401 with the vaporized mixture of acetic acid and acetic anhydride; tank 702 becomes a "collection tank" for collecting the mixture of lactic acid and acetic acid from column 401; finally, tank 703 (which already contains the mixture of lactic acid and acetic acid previously collected from column 401) is fed with acetic anhydride 102 and becomes a "reaction tank".

As the skilled person will appreciate, the above embodiment may be performed with more than three parallel reactor tanks, to further increase the flexibility of the manufacturing process.

The (S)-2-acetyloxypropionic acid obtained according to the present preparation method may then be chlorinated according to known preparation methods (as disclosed for instance in EP0773925), e.g. with thionyl chloride to give the corresponding (S)-2-acetyloxypropionyl chloride, which is then purified, e.g. by distillation.

The chlorination reaction is preferably carried out in a reactor comprising a series of at least 2 CSTR reactors (Continuous Stirred-Tank Reactor), wherein each element is equipped with its own condensation unit and its own independent gas outlet allowing to reflux the thionyl chloride condensed in each unit, thus ensuring a suitable thionyl chloride concentration in every section of the plant.

The (S)-2-acetyloxypropionic acid conversion to chloride is higher than 80%, preferably higher than 90%, even more preferably higher than 95%, and this is achieved with a residence time of about 3 hours. This is achieved by the use of chlorination reactors in a series of 2 and even more preferably of at least 3, or 4, or 5, or 6 CSTRs, each one endowed with its own condensation unit and its own independent gas outlet and with $SOCl_2$ recycling into the starting chlorination reactor.

The chlorination reaction c) also produces hydrochloric acid and sulfurous anhydride ($SO_2$ and HCl) as by-products that leave the reactor under the gas form. Also thionyl chloride produces vapours, recovered, as disclosed above, by one or more condensation units. Actually, while hydrochloric acid and sulfurous anhydride are to be disposed off, thionyl chloride is recovered, re-condensed and recycled into the starting element.

In a preferred embodiment the acidic gases coming from the chlorination reactor and from the next distillation column are treated before their emission to cut down hydrochloric acid, sulfurous anhydride, acetyl chloride and possible traces of thionyl chloride.

The chlorination reaction of (S)-2-acetyloxypropionic acid in continuous, in particular by the CSTRs cascade, is particularly advantageous in comparison to the batch process for at least two reasons: the production of the acidic gases occurs at a constant flow rate thus allowing the cutting-down system to work under stationary conditions with a clear advantage for the process safety; furthermore, thionyl chloride, which is also extremely dangerous, is recovered and recycled without significant dispersion or loss.

(S)-2-acetyloxypropionyl chloride is then isolated from the mixture obtained at the end of the chlorination reaction preferably by distillation, carried out in two steps. Accordingly, the low-boiling impurities are removed first, then the high-boiling ones, like the residual 2-acetyloxypropionic acid and the oligomers of the (S)-2-acetyloxypropionyl chloride.

(S)-2-acetyloxypropionyl chloride is thus obtained as a substantially pure product after the second distillation, with minimal amounts of impurities (Thionyl chloride: ≤1.0%; Acetyl chloride: 0.2%; Lactyl chloride/others: ≤2.0%) and is thus suitable for the synthesis of iodinated contrast agents for diagnostic use in vivo, according to the requirements of the European Pharmacopoeia presently in force.

A continuous reaction cycle, carried out on an industrial plant (production >80 kg/h, preferably >100 kg/h, up to 500 kg/h) has typically an overall yield higher than 90% and is therefore suitable for a large scale production of (S)-2-acetyloxypropionyl chloride, with the same purity grade of the final product achieved with former industrial methods and suitable for Iopamidol production under the presently in force European Pharmacopoeia.

The following examples will illustrate some specific embodiments of the inventions.

EXAMPLES

Example 1

Simulation of a Process Performed in an Assembly According to FIG. 4.

The process in accordance with the invention, in the embodiment shown in FIG. 4, was simulated using ASPEN PLUS®. Vapor-liquid equilibrium data have been calculated using UNIFAC HOC equations, which proved accurate in reproducing vapor liquid equilibrium experimental data sets.

Reactions have been calculated on the basis of rate constants as experimentally measured.

The simulated assembly has been fed with about 230 kg/h of a commercial aqueous solution of lactic acid containing about 102 kg/h of lactic acid (44% w/w), along with 6.1 kg/h of its dimer. This scale is suitable for an industrial scale production of (S)-2-acetyloxypropionic acid.

The simulated asembly has been fed with about 163 kg/h of acetic anhydride, corresponding to about 1.13 mol/mol lactic acid (about 1.10 mol/mol when referred to the sum of lactic acid and its dimer).

Volume of stirred reactor 408 has been set to 1000 L; volume of catalytic bed 409 has been set to 50 L. Reaction speed in the catalytic bed has been calculated using rate constant as determined experimentally on lab scale on a bed of Rohm &Haas Amberlyst 15°.

Column 401 top pressure have been set to 35 mbar, while the pressure of the bottom of column 402 has been set to 50 mbar: column 401 has been assigned eight theoretical plates, while column 402 has been assigned one theoretical plates. Reaction mixture has been cooled to 40° C. on cooler 410 before feeding it to the catalytic bed 409.

Table 1 below reports mol and mass flows calculated for main streams in the plant.

In particular, 103 is the product stream: comparison between this stream and stream 101 shows that conversion to lactic acid to (S)-2-acetyloxypropionic acid is practically complete. Calculated duties for the reboiler 403 and reactor 408 are 41 and 39 kW respectively.

Table 1 also shows calculated temperatures for main streams. Pressure and temperature conditions are easily feasible on industrial scale, as well as the size of the equipment.

TABLE 1

| | | Stream number (see FIG. 5) | | | | | | |
|---|---|---|---|---|---|---|---|---|
| | | 101 | 301 | 104 | 102 | 302 | 103 | 303 |
| Phase: | | Liquid | Liquid | Liquid | Liquid | Liquid | Liquid | Vapor |
| | | Component Mole Flow | | | | | | |
| Lactic Acid | kmol/hr | 1.13 | 1.13 | 0.00 | 0.00 | 0.00 | 0.00 | 0.00 |
| Acetic Acid | kmol/hr | 0.00 | 1.18 | 1.28 | 0.00 | 2.31 | 0.06 | 2.24 |
| Acetic Anhydride | kmol/hr | 0.00 | 1.59 | 0.00 | 1.28 | 1.73 | 0.07 | 1.67 |
| H2O | kmol/hr | 6.75 | 0.00 | 6.70 | 0.00 | 0.00 | 0.00 | 0.00 |
| (S)-2-acetyloxypropionic acid | kmol/hr | 0.00 | 0.00 | 0.00 | 0.00 | 1.13 | 1.13 | 0.00 |
| (S)-2-lactoyloxypropionic acid (Dimer) | kmol/hr | 0.04 | | | | 0.02 | 0.00 | |
| Acetylated Dimer | kmol/hr | 0.00 | | | | 0.02 | 0.03 | |
| | | Component Mass Flow | | | | | | |
| Lactic Acid | kg/hr | 101.8 | 101.8 | 0.0 | 0.0 | 0.1 | 0.1 | 0.0 |
| Acetic Acid | kg/hr | 0.0 | 70.6 | 76.6 | 0.0 | 138.4 | 3.6 | 134.8 |
| Acetic Anhydride | kg/hr | 0.0 | 162.8 | 7.3 | 130.7 | 176.2 | 6.7 | 170.2 |
| H2O | kg/hr | 121.6 | 0.0 | 120.7 | 0.0 | 0.0 | 0.0 | 0.0 |
| (S)-2-acetyloxypropionic acid | kg/hr | 0.0 | 0.1 | 0.0 | 0.0 | 149.2 | 149.1 | 0.1 |
| (S)-2-lactoyloxypropionic acid (Dimer) | kg/hr | 6.1 | | | | 2.7 | 0.5 | |
| Acetylated Dimer | kg/hr | 0.0 | | | | 4.2 | 7.0 | |
| Mole Flow | kmol/hr | 7.92 | 3.90 | 7.98 | 1.28 | 5.20 | 1.29 | 3.91 |
| Mass Flow | kg/hr | 229.5 | 335.3 | 204.6 | 130.7 | 470.8 | 167.1 | 305.0 |
| Temperature | ° C. | 25 | 62 | 20 | 25 | 70 | 114 | 42 |

Example 2

Simulation of a Process Performed in an Assembly According to FIG. 5.

The application of the process carried out in accordance with the invention, in the embodiment showed in FIG. 5, was simulated using ASPEN PLUS® with the same vapor liquid equilibrium relationships of example 1. The device has been fed with the same streams of example 1.

Volume of stirred reactor 408 has been kept at 1000 L; volume of reactor 10 has been set to 300 L.

Column 401 top pressure have been set to 50 mbar, while the pressure of the bottom of column 402 has been set to 70 mbar: column 401 has been assigned ten theoretical plates, while column 402 has been assigned two theoretical plate.

Composition of streams and duties of the reboiler and reactor do not change significantly when compared to example 1: bottom temperature of column 402 has been kept to 130° C. in this case, obtaining an increased concentration of (S)-2-acetyloxypropionic acid (93%).

Example 3

Pilot Scale Preparation of (S)-2-Acetyloxypropionic Acid

A 50% commercial solution of lactic acid in water, containing 46.5% lactic acid monomer and 3.2% (w/w) dimer, was fed to the 10$^{th}$ tray, starting the count from the head, of an Oldershaw distillation column having the diameter of 5 cm, equipped with 30 perforated trays. A stream of acetic anhydride was fed to the thermosiphon reboiler, which has a liquid hold-up of 1.5 L. The flow rates of the two feedings were, respectively, of 544 and 750 g/h. The column head pressure and temperature were respectively 32 mbar and 37° C. Distillate was condensed and collected (i.e. no distillate was refluxed to the top of the column).

The distillate flow rate was about 600 g/h. The head product contained only water and acetic acid.

The mixture obtained from the reboiler with a flow rate of about 690 g/h contained 42.7% of acetic acid and the remainder 57.3% containing the following percentages of product (w/w):

| | |
|---|---|
| Lactic acid | 14.77% |
| Lactic acid dimer + residual acetic anhydride | 7.78% |
| (S)-2-acetyloxypropionic acid | 71.69% |
| Acetylated lactic acid dimer | 5.75% |

This product was cooled to 45° C. and fed to a glass column having a 4 cm diameter, equipped with a thermostatic jacket and a porous glass disc at the bottom, containing 30 g of Amberlyst® 15, a sulfonic resin in its acid form with 4.7 meq/g of sulfonic groups. The outlet reactor temperature was 75° C. and a solution, containing 43.5% of acetic acid, with the remainder 56.5% containing:

| | |
|---|---|
| Lactic acid | 0.17% |
| Residual acetic anhydride | 4.13% |
| (S)-2-acetyloxypropionic acid | 88.77% |
| Acetylated lactic acid dimer | 6.92% |

The obtained solution was fed to an Oldershaw distillation column having the diameter of 3 cm, equipped with 5 perforated plates equipped with a 600 mL glass stirred jacketed reactor as a reboiler; the feed was at the first plate (starting the count from the head), with a rate of 600 g/h. The reboiler temperature was about 130° C. and the pressure 59 mbar.

The head product was constituted by acetic anhydride and acetic acid; the distillate flow rate was 318 g/h.

The product, obtained from the reboiler with a flow rate 390 g/h, had the following composition (% w/w):

| | |
|---|---|
| Acetic acid | 1.50 |
| Lactic acid | 0.0 |
| Residual acetic anhydride | 0.5 |
| (S)-2-acetyloxypropionic acid | 90.91 |
| Acetylated lactic acid dimer | 7.09 |

Overall yield of the run was 96%.

Example 4

Simulation of a Process Performed in an Assembly According to FIG. 7.

The application of the process carried out in accordance with the invention, in the embodiment showed in FIG. 7, was numerically simulated with the same vapor liquid equilibrium relationships of example 1. The device has been fed with the same streams of example 1.

In this example, three jacketed stirred tanks perform a cycle comprising:
  a step in which the tank is loaded with the S-lactic acid and acetic acid solution from the bottom of column 401;
  a reaction step, in which acetic anhydride is loaded into the tank and is reacted with lactic acid
  a distillation step, in which acetic acid and the excess of acetic anhydride are distilled from the tank, and resulting vapor stream is fed at the bottom of column 401.

At a given time, each of the reactor performs a differing step.

Column 401 is continuously fed from its top with a S-lactic acid solution, containing 40% of lactic acid and 3% of dimer on weight basis (typical commercial solution), and from the bottom with the acetic acid+acetic anhydride vapor sequentially produced by 1 out of the 3 above jacketed stirred tank; the column continuously discharges the bottom liquid toward one of the 3 above jacketed stirred tanks.

Volume of stirred jacketed tanks 701, 702 and 703 has been kept at 3000 L.

Column 401 top pressure have been set to 50 mbar: column 401 has been assigned 10 theoretical plates.

Start up is performed by loading 1400-2000 L of acetic acid in stirred jacketed tank 702: tank 702 is heated by steam and vapour is directed to column 401. When temperature at the top of column 401 increases, indicating that acetic acid vapors filled the equipment, the lactic acid solution feed is started and gradually increased to 183.4 kg/h and steam to jacket of tank 702 is adjusted to control distillate (stream #104) flowrate to 275 kg/h.

Liquid from the bottom of the column, composed by lactic acid and acetic acid is collected in jacketed stirred tank 701 (time 0). After 5 hours, amount of solution collected in tank 701 reaches 1400 kg: at this point, liquid stream from the bottom of column 401 is switched to tank 703; simultaneously, 497 kg acetic anhydride are added in tank 701, thus starting acetylation reaction. After 3 h (8 h from time 0), reaction is completed and stirred jacketed tank 701 is heated with steam to start distillation: vapor generated by distillation, which is made of acetic acid and acetic anhydride, is directed to the column 401 and is controlled as previously described for tank 702. As soon as distillation from tank (8) is started, steam to jacket of tank 702 is closed and the tank is ready to receive the bottom liquid from the column. At 10 h from time 0, liquid stream from the bottom of column 401 is switched from tank 703 to tank 702; simultaneously, 497 kg acetic anhydride are added in tank 703, thus starting acetylation reaction in tank 703. At 13 h from time 0, acetylation reaction in tank 703 is completed and stirred jacketed tank 703 is heated with steam to start distillation. At the same time, residual amount of acetic acid and acetic anhydride in reactor 701 are too low to give a sufficient vapour flowrate and temperature has reached 114° C.: the distillation is stopped by switching steam to jacket off and the solution contained in the reactor, essentially consisting of (S)-2-acetyloxypropionic acid, is cooled down to 50° C. and then collected to the product tank, while jacketed stirred tank 701 is ready to restart the cycle from the beginning. A new identical cycle can be started 15 h after time 0.

Overall yield is 98% (referred to S-lactic acid). Composition of streams (referring to the second or following production cycle) amount per batch are reported in the following table: productivity can be calculated taking into account that, according to the described arrangement, the device produces a batch every 5 hours.

Details of the process are reported in table 2 below

The excess of acetic anhydride and the acetic acid, formed as reaction by product, were removed by distillation (85° C., 20 mbar) and the obtained product had the following composition:

| Component | % (mol/mol) |
|---|---|
| (S)-2-acetyloxypropionic acid | 55.1 |
| Acetylated lactic acid dimer | 32.7 |
| Acetylated lactic acid trimer | 9.7 |
| Other impurities | 2.5 |

The comparison between the results of present example and Example 3 shows that direct acetylation of lactic acid requires a large excess of acetic anhydride (1.64 equivalents

TABLE 2

| | | Stream number (see FIG. 7) | | | | | |
|---|---|---|---|---|---|---|---|
| | | 101 | 102 | 301 | 303 | 104 | 103 |
| Phase: | | Liquid | Liquid | Liquid | Vapor | Liquid | Liquid |
| Component Mole Quantities | | | | | | | |
| Acetic Acid | kmol | 0.00 | 0.00 | 18.45 | 22.65 | 4.20 | 0.34 |
| Acetic Anhydride | kmol | 0.00 | 4.87 | 7.17 | 7.17 | 0.00 | 0.32 |
| Lactic Acid | kmol | 4.49 | 0.00 | 4.49 | 0.00 | 0.00 | 0.09 |
| (S)-2-lactoyloxypropionic acid (Dimer) | kmol | 0.15 | 0.00 | 0.15 | 0.00 | 0.00 | 0.00 |
| Acetylated Dimer | kmol | 0.00 | 0.00 | 0.00 | 0.00 | 0.00 | 0.14 |
| (S)-2-acetyloxypropionic acid | kmol | 0.00 | 0.00 | 0.00 | 0.00 | 0.00 | 4.40 |
| H2O | kmol | 27.11 | 0.00 | 0.00 | 0.00 | 27.11 | 0.00 |
| Mass Quantities | | | | | | | |
| Acetic Acid | kg | 0.0 | 0.0 | 1107.9 | 1360.2 | 252.2 | 20.7 |
| Acetic Anhydride | kg | 0.0 | 497.1 | 732.4 | 732.4 | 0.0 | 33.1 |
| Lactic Acid | kg | 404.6 | 0.0 | 404.6 | 0.0 | 0.0 | 8.1 |
| (S)-2-lactoyloxypropionic acid (Dimer) | kg | 23.8 | 0.0 | 23.8 | 0.0 | 0.0 | 0.5 |
| Acetylated Dimer | kg | 0.0 | 0.0 | 0.0 | 0.0 | 0.0 | 29.4 |
| (S)-2-acetyloxypropionic acid | kg | 0.0 | 0.0 | 0.0 | 0.0 | 0.0 | 581.4 |
| H2O | kg | 488.6 | 0.0 | 0.0 | 0.0 | 488.6 | 0.0 |
| Mole Amount | kmol | 31.75 | 4.87 | 30.26 | 29.83 | 31.31 | 5.31 |
| Mass Amount | kg | 917.0 | 497.1 | 2268.8 | 2092.6 | 740.8 | 673.2 |
| Temperature | ° C. | 25 | 25 | 62 | 62-114 | 20 | 50 |

Example 5

Comparative Example (U.S. Pat. No. 2,399,595)

The acetylation was carried out according to the procedure reported in U.S. Pat. No. 2,399,595, using a 88% solution of aqueous lactic acid, which is the highest concentration commercially available.

Sulfuric acid (0.4 mL) was added to 150 g of 88% aqueous lactic acid keeping the mixture under stirring and the temperature below 25° C.; then acetic anhydride (250 g) was slowly added.

The mixture was kept at room temperature for 16 h and then heated to reflux for 1 h.

At the end 1 g of sodium acetate was added and the mixture was filtered.

instead of 1.25) and leads to a product highly contaminated by oligomeric impurities, unless performed according to the present invention.

Example 6

Chlorination of (S)-2-acetyloxypropionic acid (S)-2-acetyloxypropionic acid, obtained as described in example 3, was fed together with thionyl chloride into a series of 3 continuous reactors of about the same volume, each one equipped with its own reflux condensation unity. The condensate from each condensation unity was completely refluxed to the corresponding stirred reactor. The total volume of the 3 reactors was 4000 mL.

The feeding flow rate of the solution into the first reactor was about 800 g/h. Into the first reactor was also fed thionyl chloride at a flow rate of about 900 g/h. The feeding molar ratio between thionyl chloride and acetyloxypropionic acid was 1.37 moles/mole.

Once reached the steady state, the temperature of the first reactor was about 60° C., the one of the second 66° C. and the one of the third 74° C.

The raw chlorination product obtained was directed at about 0.35 kg/h to the 13$^{th}$ tray of a first continuous distillation Oldershaw column having a diameter of 30 mm, carrying 25 perforated trays, working at an head pressure of 25 Torr, operated with a reflux rate of about 3:1, in which the head light products, acetyl chloride and thionyl chloride, were removed obtaining from the reboiler a (S)-2-acetyloxy-propionylchloride devoid of volatile products. Head temperature was about 35° C., while bottom temperature was about 88° C. The product from the reboiler was fed to the 20$^{th}$ tray starting from the head of a second continuous distillation column having a diameter of 30 mm, carrying 25 perforated plates, head-separating a product with a assay of 99.7% (gas chromatography). Reflux ratio was set to 2:1, head pressure was kept to 11 Torr, while bottom temperature was about 90° C.

The invention claimed is:

1. A method for preparing an (S)-2-acetyloxypropionic acid in a preparation assembly comprising a distillation section (A) and a reaction section (B), the distillation section (A) comprising a top portion and a bottom portion connected to said reaction section (B), the method comprising the steps of:
   a. continuously feeding an aqueous solution of a lactic acid to the top portion of the distillation section (A);
   b. feeding an acetic anhydride into the reaction section (B);
   c. reacting the lactic acid with the acetic anhydride in the reaction section (B), thus forming the (S)-2-acetyloxy-propionic acid and an acetic acid;
   d. evaporating a vapor mixture of the acetic acid and of the unreacted acetic anhydride from the reaction section (B);
   e. feeding the vapor mixture of step d to the distillation section (A) for stripping water from the aqueous solution of lactic acid to form a substantially anhydrous lactic acid which counterflows through said distillation section (A) towards the reaction section (B), so that a mixture of the substantially anhydrous lactic acid and the acetic acid enters the reaction section (B) from the bottom portion of the distillation section (A);
   f. recovering the (S)-2-acetyloxypropionic acid from the reaction section (B); and
   g. collecting a diluted aqueous solution of the acetic acid at the top portion of the distillation section (A).

2. The method according to claim 1, wherein the reaction section (B) of the preparation assembly comprises two separate sub-sections (B') and (B"), wherein the sub-section (B') is dedicated to performing an acetylation reaction between the lactic acid and the acetic anhydride, and sub-section (B") is dedicated to evaporation and feeding of the acetic acid and the unreacted acetic anhydride to the distillation section (A).

3. The method according to claim 1, wherein the preparation assembly is under a negative pressure.

4. The method according to claim 3, wherein the negative pressure is between 5 mbar and 200 mbar.

5. The method according to claim 1, wherein the aqueous solution of the lactic acid has a concentration from 20% to 90% (w/w) of lactic acid.

6. The method according to claim 1, wherein the molar ratio between the acetic anhydride and the lactic acid in step c is from 1.01 to 1.5.

7. The method according to claim 1, wherein the vapor mixture of step d is fed continuously to the distillation section (A).

8. The method according to claim 1, wherein the reaction section (B) comprises at least two stirred jacketed reactor tanks.

9. The method according to claim 1, wherein the reaction section (B) comprises at least three stirred jacketed reactor tanks.

10. The method according to claim 1, wherein the lactic acid is reacted with the acetic anhydride in the presence of a solid acidic catalyst.

11. The method according to claim 1, further comprising the step of reacting the (S)-2-acetyloxypropionic acid with a thionyl chloride to give a (S)-2-acetyloxypropionyl chloride.

12. The method according to claim 2, wherein the aqueous solution of the lactic acid has a concentration from 20% to 90% (w/w) of lactic acid.

13. The method according to claim 2, wherein the reaction section (B) comprises at least a first tank and a second tank, wherein: (i) the first tank, which is continuously fed with the acetic anhydride and with a mixture of the lactic acid and the acetic acid from the distillation section (A), performs the acetylation reaction; and (ii) the second tank is dedicated to the evaporation of the vapor mixture of the acetic acid and the unreacted acetic anhydride from a completed reaction mixture, the vapor mixture being continuously fed to the distillation section (A).

14. The method according to claim 2, wherein the reaction section (B) comprises at least a first tank, a second tank, and a third tank, wherein: (i) the first tank, which has been previously fed with the acetic anhydride and with a mixture of the lactic acid and the acetic acid from the distillation section (A), is dedicated to performing the acetylation reaction in a batch mode; (ii) the second tank is dedicated to the evaporation of the vapor mixture of the acetic acid and the unreacted acetic anhydride from a completed reaction mixture, the vapor mixture being continuously fed to the distillation section (A); and (iii) the third tank is dedicated to collecting a mixture of the lactic acid and the acetic acid continuously flowing from the distillation section (A).

15. The method according to claim 12, wherein the reaction section (B) comprises at least a first tank, a second tank, and a third tank, wherein: (i) the first tank, which has been previously fed with the acetic anhydride and with a mixture of the lactic acid and the acetic acid from the distillation section (A), is dedicated to performing the acetylation reaction in a batch mode; (ii) the second tank is dedicated to the evaporation of the vapor mixture of the acetic acid and the unreacted acetic anhydride from a completed reaction mixture, the vapor mixture being continuously fed to the distillation section (A); and (iii) the third tank is dedicated to collecting a mixture of the lactic acid and the acetic acid continuously flowing from the distillation section (A).

16. The method according to claim 14, wherein the first tank, the second tank, and the third tank are interchangeable with one another.

17. The method according to claim 15, wherein the first tank, the second tank, and the third tank are interchangeable with one another.

18. The method according to claim 15, wherein the molar ratio between the acetic anhydride and the lactic acid in step c is from 1.01 to 1.5.

* * * * *